US008676295B2

(12) United States Patent
Cunningham et al.

(10) Patent No.: US 8,676,295 B2

(45) Date of Patent: Mar. 18, 2014

(54) INTERVENTIONAL INSTRUMENT TRACKING DEVICE IMAGEABLE WITH MAGNETIC RESONANCE IMAGING AND METHOD FOR USE THEREOF

(75) Inventors: Charles H. Cunningham, Toronto (CA); William Dominquez-Viqueira, Toronto (CA)

(73) Assignee: Sunnybrook Health Sciences Center, Toronto (CA)

( * ) Notice: Subject to any disclaimer, the term of this patent is extended or adjusted under 35 U.S.C. 154(b) by 17 days.

(21) Appl. No.: 13/518,160

(22) PCT Filed: Dec. 22, 2010

(86) PCT No.: PCT/CA2010/002041

§ 371 (c)(1), (2), (4) Date: Aug. 20, 2012

(87) PCT Pub. No.: WO2011/075839

PCT Pub. Date: Jun. 30, 2011

(65) Prior Publication Data

US 2012/0310080 A1 Dec. 6, 2012

Related U.S. Application Data

(60) Provisional application No. 61/289,271, filed on Dec. 22, 2009.

(51) Int. Cl.
*A61M 25/095* (2006.01)
*A61B 5/055* (2006.01)

(52) U.S. Cl.
USPC ........... 600/414; 600/411; 600/420; 600/421; 600/422; 600/423; 600/424

(58) Field of Classification Search
USPC .................................. 600/411, 414, 420–424
See application file for complete search history.

(56) References Cited

U.S. PATENT DOCUMENTS

| | | | | |
|---|---|---|---|---|
| 6,430,429 | B1 * | 8/2002 | Van Vaals | 600/410 |
| 2005/0113659 | A1 * | 5/2005 | Pothier et al. | 600/372 |
| 2012/0268127 | A1 * | 10/2012 | Cunningham et al. | 324/309 |

FOREIGN PATENT DOCUMENTS

| | | |
|---|---|---|
| EP | 0 775 500 | 5/1997 |
| WO | 97/17622 | 5/1997 |
| WO | 00/33099 | 6/2000 |

OTHER PUBLICATIONS

Debatin et al., "Interventional Magnetic Resonance Imaging". Medical Radiology. Diagnositic Imaging and Radiation Oncology. © Springer Berlin Heidelberg. 1998.*

International Search Report as mailed on Apr. 4, 2011 for International Application No. PCT/CA2010/002041.

* cited by examiner

*Primary Examiner* — Long V. Le
*Assistant Examiner* — Colin T Sakamoto
(74) *Attorney, Agent, or Firm* — Quarles & Brady, LLP

(57) ABSTRACT

A tracking device configured to be coupled to an interventional instrument and tracked by a magnetic resonance imaging system is provided. The tracking device includes, for example, paramagnetic and diamagnetic components that form first and second tracking members. When the tracking device is adjusted into a first arrangement, the tracking device will produce a local magnetic field in the presence of the magnetic field of an MRI system that is measurable by the MRI system. However, when the tracking device is adjusted into a second arrangement, the local magnetic field produced by the tracking device is reduced relative to the first arrangement, wherein the reduced local magnetic field produces substantially no magnetic field disturbances detectable by the MRI system. Images may be acquired of a patient in which the tracking device has been introduced and, using a numerical fitting method, an accurate location of the tracking device can be determined.

20 Claims, 9 Drawing Sheets

113 124 126 102 104 106 108 112 116 100 110 114 118 122 113 120

INTERVENTIONAL INSTRUMENT TRACKING DEVICE IMAGEABLE WITH MAGNETIC RESONANCE IMAGING AND METHOD FOR USE THEREOF

CROSS-REFERENCE TO RELATED APPLICATIONS

This application represents the U.S. National Stage of International Application No. PCT/CA2010/002041, filed Dec. 22, 2010, which claims the benefit of U.S. Provisional Patent Application Ser. No. 61/289,271 filed on Dec. 22, 2009, and entitled "System and Method for Interventional MRI Device Tracking with Mechanically Controlled Susceptibility Effects." The foregoing applications are incorporated herein by reference in their entirety.

BACKGROUND OF THE INVENTION

The field of the invention is magnetic resonance imaging ("MRI") systems and methods. More particularly, the invention relates to systems and methods for tracking an interventional device that can be actuated to induce measurable susceptibility effects.

The placement of interventional devices, such as guidewires and stents, using MRI guidance is a promising and evolving field with great clinical potential. One particular challenge of this field, however, has been how to develop safe and reliable methods for tracking such devices as they are moved and manipulated within vessels or organs. The tips of guidewires can be easily visualized using conventional x-ray fluoroscopy by applying small, radio-opaque markers to the tips. In MRI, the analog to the radio-opaque marker is a marker made of a material with a sufficiently large magnetic susceptibility, relative to the surrounding tissues, such as a stainless steel tip on a nitinol wire. In MR images depicting a guidewire containing such markers, a local hypointense region is present in the tissues adjacent to the markers, thereby resulting in a loss of clinically relevant information. Exemplary MR visible interventional instruments of this kind are described, for example, in U.S. Pat. Nos. 5,728,079 and 6,430,429.

The interventional instrument described in U.S. Pat. No. 5,728,079 is a catheter provided with a hollow tubular holder, and in which the indicator element includes a concentric layer of a paramagnetic material. The concentric paramagnetic layer is provided in the form of a cylindrical sheath whose longitudinal axis is coincident with the longitudinal axis of the holder. The paramagnetic material influences the magnetic resonance image of a patient to be examined by means of an MRI system. The influence the device has on MR images makes it possible to determine the position of the interventional instrument within the body of the patient without the instrument being directly visible. However, the influence of the paramagnetic component in the device on the MR image adversely affects the diagnostic quality of the magnetic resonance image. As a result of the influence of the indicator element, MR images will exhibit degraded or lost anatomical details in the regions adjacent to the indicator element.

The interventional instrument described in U.S. Pat. No. 6,430,429 includes an indicator element for which the degree of influencing of the magnetic resonance image is adjustable, notably by rotation of the indicator element relative to the direction of the steady magnetic field of the MRI system. For example, the indicator element is a paramagnetic strip which may include several segments of different magnetic susceptibility. Only paramagnetic components are described in U.S. Pat. No. 6,430,429. Thus, the influence of this device on a magnetic resonance image will depend on the orientation of the device relative to the magnetic field of the MRI system. However, this adjustability of the device's influence is limited, and while the degree of the device's influence on MR images can be reduced, it cannot be eliminated and signal loss will still occur even with this reduced influence.

Despite being easy to locate in MR images and relatively inexpensive and safe, the aforementioned interventional devices produce a loss of signal in the vicinity of the indicator element that, in turn, obscures the desired region of interest: the tissue adjacent to the tip of the device. Thus, while the location of the tips of the aforementioned devices can be easily identified, the nature of the tissue that the devices are being moved through is obscured by the same effect that allows the visualization of the devices.

It would therefore be desirable to provide an interventional device that can be accurately located in an MR image while also allowing visualization of the tissue adjacent to the device by mitigating signal losses.

SUMMARY OF THE INVENTION

The present invention overcomes the aforementioned drawbacks by providing a tracking device that can be imaged with magnetic resonance imaging (MRI). The tracking device generally includes two or more tracking members having different magnetic susceptibilities. The tracking device can be adjusted between a first arrangement that produces a local magnetic field external to the tracking device when a magnetic field, such as the magnetic field of an MRI system, is applied to the tracking device, and a second arrangement where the local magnetic field external to the tracking device is reduced relative to the first arrangement. These arrangements may be referred to generally as an "on" and "off" configuration, respectively. The tracking device operates to produce a measurable local magnetic field in the "on" configuration and a reduced local magnetic field in the "off" configuration, regardless of the orientation of the tracking device relative to the magnetic field of the MRI system.

It is an aspect of the invention to provide a tracking device configured to be coupled to an interventional medical device to track a position of the interventional medical device during an interventional medical procedure using an MRI system. The tracking device includes a first tracking member having a first magnetic susceptibility and configured to be coupled to the interventional medical device, and a second tracking member having a second magnetic susceptibility, which is different than the first magnetic susceptibility, and configured to be coupled to the interventional medical device. The first tracking member may include at least one paramagnetic component and the second tracking member may include at least one diamagnetic component. For example, the first tracking member may include one, two, or more paramagnetic components, and the second tracking member may include one, two, or more diamagnetic components. At least one of the first tracking member and the second tracking member is configured to adjust relative to the other of the first tracking member and the second tracking member to adjust the tracking device between a first arrangement and a second arrangement. When the first and second tracking members include more than one component, these components can be independently adjusted relative to each other to adjust the tracking device between the first and second arrangements. The first and second magnetic susceptibilities are selected such that when the tracking device is positioned within a magnetic field of an MRI system the tracking device produces a local magnetic field that is measurable by the MRI system when the tracking device is arranged in the first arrangement, and the tracking device produces a local magnetic field that is reduced with respect to the local magnetic field produced by the tracking device in the first arrangement when the tracking device is arranged in the second arrangement. Thus, in the first arrangement, the tracking device produces a magnetic field disturbance that is measurable with the MRI system, whereas in the second arrangement, magnetic field disturbances from the tracking device that may be detected with the MRI system are substantially suppressed.

It is another aspect of the invention to provide a catheter device for use with an MRI system. The catheter device includes a tracking device containing a first annular component having a first magnetic susceptibility and a second annular component having a second magnetic susceptibility that is different than the first magnetic susceptibility. A wire is coupled to the tracking device and extends away from the tracking device through a catheter tube that is also coupled to the tracking device. The wire is configured such that when it is actuated, at least one of the first and second annular components moves relative to the other, thereby altering local magnetic fields produced by the tracking device when the tracking device is positioned in a magnetic field of an MRI system. The catheter device may include a driver coupled to the wire for actuating the wire, and the driver may be in communication with a processor that is configured to synchronously operate the driver in response to a pulse sequence performed by the MRI system.

It is yet another aspect of the invention to provide a method for monitoring an interventional procedure with an MRI system and an interventional instrument that includes a tracking device having a plurality of concentric components of opposing magnetic susceptibilities that are movably engaged with each other. The method includes the step of manipulating the tracking device so that its concentric components are axially aligned, thereby substantially suppressing magnetic field disturbances produced by the tracking device. While the interventional device is positioned within a patient, the MRI system is operated to obtain a first set of images of a patient. As these images are obtained, magnetic field disturbances produced by the tracking device are substantially suppressed. The interventional device may be manipulated then to produce a measurable magnetic field disturbance by axially displacing the concentric components of the tracking device relative to one another. A second set of images of the patient is then obtained with the MRI system while the interventional device is producing the measureable magnetic field disturbance. From the first and second set of images, a position of the interventional device is determined.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Figure 1:
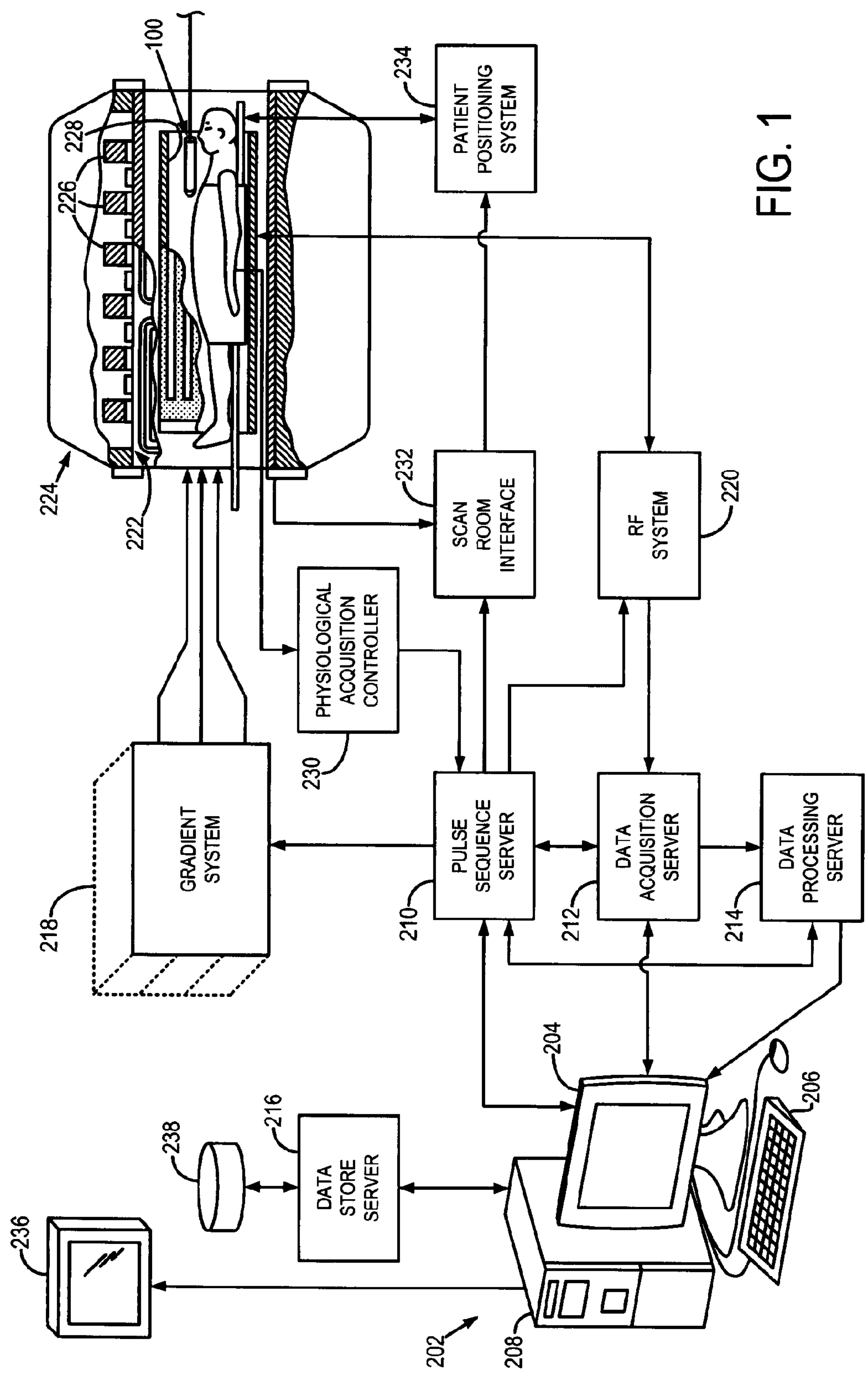
FIG. 1 is a block diagram of an exemplary magnetic resonance imaging ("MRI") system for tracking a tracking device of the present invention.

With initial reference to FIG. 1, a tracking device 100 for tracking an interventional instrument during a medical procedure with a magnetic resonance imaging ("MRI") system is provided. Generally, the tracking device 100 includes two or more tracking members having different magnetic susceptibilities. As will be described in detail below, each tracking member may include one or more components having similar magnetic susceptibilities, with different tracking member having different magnetic susceptibilities, in general. The components may include concentric cylindrical and annular components, radial sectors, annular discs, or other such shapes, as will be discussed below. The tracking members can be adjusted between a first configuration that produces a local magnetic field external to the device in the presence of an applied magnetic field, such as the magnetic field of an MRI system, and a second configuration where the local magnetic field produced external to the device is reduced relative to the first configuration. These configurations may be referred to generally as "on" and "off" configurations, respectively. The tracking device operates to produce a measurable local magnetic field regardless of the orientation of the tracking device relative to the magnetic field of the MRI system.

Materials with positive magnetic susceptibility, such as paramagnetic materials, become magnetized when exposed to an applied magnetic field, with the vector direction of that magnetization being in the same direction as the applied magnetic field. In contrast, materials with negative magnetic susceptibility, such as diamagnetic materials, become magnetized with the vector direction of that magnetization in the opposite direction to that of the applied magnetic field. With the tracking device 100 of the present invention, magnetic fields from components of opposing magnetic susceptibility significantly oppose each other to reduce the overall local magnetic field produced by the tracking device when the tracking device is in an "off" configuration, thereby allowing the acquisition of magnetic resonance images with minimal signal loss from the tracking device 100. When the device is adjusted into an "on" configuration, the paramagnetic and diamagnetic components are moved relative to each other such that their magnetic fields no longer significantly oppose each other. The result of this relative spacing of the components is that a larger magnetic field disturbance is created when the device is in the "on" position than when the device is in the "off" position, thereby rendering the tracking device visible in images acquired with an MRI system.

Referring particularly now to FIG. 1, an exemplary MRI system 200 for imaging and determining the position of the catheter tracking device 100 is illustrated. The MRI system 200 includes a workstation 202 having a display 204 and a keyboard 206. The workstation 202 includes a processor 208, such as a commercially available programmable machine running a commercially available operating system. The workstation 202 provides the operator interface that enables scan prescriptions to be entered into the MRI system 200. The workstation 202 is coupled to four servers: a pulse sequence server 210; a data acquisition server 212; a data processing server 214, and a data store server 216. The workstation 202 and each server 210, 212, 214 and 216 are connected to communicate with each other.

The pulse sequence server 210 functions in response to instructions downloaded from the workstation 202 to operate a gradient system 218 and a radiofrequency ("RF") system 220. Gradient waveforms necessary to perform the prescribed scan are produced and applied to the gradient system 218, which excites gradient coils in an assembly 222 to produce the magnetic field gradients $G_x$, $G_y$, and $G_z$ used for position encoding MR signals. The gradient coil assembly 222 forms part of a magnet assembly 224 that includes a polarizing magnet 226 and a whole-body RF coil 228.

RF excitation waveforms are applied to the RF coil 228, or a separate local coil (not shown in FIG. 1), by the RF system 220 to perform the prescribed magnetic resonance pulse sequence. Responsive MR signals detected by the RF coil 228, or a separate local coil (not shown in FIG. 1), are received by the RF system 220, amplified, demodulated, filtered, and digitized under direction of commands produced by the pulse sequence server 210. The RF system 220 includes an RF transmitter for producing a wide variety of RF pulses used in MR pulse sequences. The RF transmitter is responsive to the scan prescription and direction from the pulse sequence server 210 to produce RF pulses of the desired frequency, phase, and pulse amplitude waveform. The generated RF pulses may be applied to the whole body RF coil 228 or to one or more local coils or coil arrays (not shown in FIG. 1).

The RF system 220 also includes one or more RF receiver channels. Each RF receiver channel includes an RF amplifier that amplifies the MR signal received by the coil 228 to which it is connected, and a detector that detects and digitizes the I and Q quadrature components of the received MR signal. The magnitude of the received MR signal may thus be determined at any sampled point by the square root of the sum of the squares of the I and Q components:

$$M=\sqrt{I^2+Q^2} \quad (1);$$

and the phase of the received MR signal may also be determined:

$$\phi = \tan^{-1}\left(\frac{Q}{I}\right). \quad (2)$$

The pulse sequence server 210 also optionally receives patient data from a physiological acquisition controller 230. The controller 230 receives signals from a number of different sensors connected to the patient, such as electrocardiograph ("ECG") signals from electrodes, or respiratory signals from a bellows or other respiratory monitoring device. Such signals are typically used by the pulse sequence server 210 to synchronize, or "gate," the performance of the scan with the subject's heart beat or respiration.

The pulse sequence server 210 also connects to a scan room interface circuit 232 that receives signals from various sensors associated with the condition of the patient and the magnet system. It is also through the scan room interface circuit 232 that a patient positioning system 234 receives commands to move the patient to desired positions during the scan. The scan room interface circuit 232 may also communicate with the tracking device 100 to direct manipulate the tracking device 100 between its "on" and "off" configurations. For example, the tracking device 100 can be programmed to operate synchronously with the repetition time ("TR") of a pulse sequence, thereby providing data acquisition of the tracking device 100 in both its "on" and "off" configurations.

The digitized MR signal samples produced by the RF system 220 are received by the data acquisition server 212. The data acquisition server 212 operates in response to instructions downloaded from the workstation 202 to receive the real-time MR data and provide buffer storage, such that no data is lost by data overrun. In some scans, the data acquisition server 212 does little more than pass the acquired MR data to the data processor server 214. However, in scans that require information derived from acquired MR data to control the further performance of the scan, the data acquisition server 212 is programmed to produce such information and convey it to the pulse sequence server 210. For example, during prescans, MR data is acquired and used to calibrate the pulse sequence performed by the pulse sequence server 210. Also, navigator signals may be acquired during a scan and used to adjust the operating parameters of the RF system 220 or the gradient system 218, or to control the view order in which k-space is sampled. The data acquisition server 212 may also be employed to process MR signals used to detect the arrival of contrast agent in a magnetic resonance angiography ("MRA") scan. In all these examples, the data acquisition server 212 acquires MR data and processes it in real-time to produce information that is used to control the scan.

The data processing server 214 receives MR data from the data acquisition server 212 and processes it in accordance with instructions downloaded from the workstation 202. Such processing may include, for example: Fourier transformation of raw k-space MR data to produce two or three-dimensional images; the application of filters to a reconstructed image; the performance of a backprojection image reconstruction of acquired MR data; the generation of functional MR images; and the calculation of motion or flow images.

Images reconstructed by the data processing server 214 are conveyed back to the workstation 202 where they are stored. Real-time images are stored in a data base memory cache (not shown in FIG. 1), from which they may be output to operator display 212 or a display 236 that is located near the magnet assembly 224 for use by attending physicians. Batch mode images or selected real time images are stored in a host database on disc storage 238. When such images have been reconstructed and transferred to storage, the data processing server 214 notifies the data store server 216 on the workstation 202. The workstation 202 may be used by an operator to archive the images, produce films, or send the images via a network to other facilities.

Because the influence on the magnetic resonance images by the tracking device 100 is adjustable by relative movement of the tracking members of the tracking device 100, the tracking members including paramagnetic and diamagnetic components, MR images that are influenced by the tracking device 100 may be acquired. The influence of the tracking device 100 on these images can be visualized and measured, such that a location of the tracking device 100 can be accurately determined. Furthermore, because the tracking device 100 can be switched between an "on" configuration, in which the tracking device 100 creates significant susceptibility artifacts allowing the location of the tracking device 100 to be determinable, but in which signals from adjacent tissues are distorted, and an "off" configuration, in which the tracking device 100 is not visible, but in which signals from adjacent tissues are minimally distorted, clinically useful images of a patient can be obtained while the tracking device 100 is positioned within a patient. For example, by adjusting the relative arrangement of the tracking members to adjust the tracking device between a second and first arrangement, the influence of the tracking device 100 on the MR images is reduced so that signal losses in tissues adjacent to the tracking device 100 due to magnetic susceptibility artifacts from the tracking device 100 are substantially suppressed. It is noted that each tracking member may include a plurality of components and that each of these components may be adjusted individually or in combination when the tracking device is adjusted between the first and second arrangement.

The tracking device 100 of the present invention generally operates by adjusting the arrangement of the tracking device by adjusting one of a first tracking member having a first magnetic susceptibility and a second tracking member having a second magnetic susceptibility relative to each other. Because of the disparate magnetic susceptibilities of these first and second tracking members, the local magnetic fields produced by the tracking device 100 in the presence of an applied magnetic field can be varied from a measurable state when the first and second tracking members are in a first arrangement, to a minimal state when the first and second tracking members are in a second arrangement. In the minimal state, the local magnetic fields produced by the first and second tracking members substantially cancel each other out, whereas in the measurable state the local magnetic fields produced by the first and second tracking members do not cancel each other out, thereby producing a magnetic field disturbance that is measurable with an MRI system. Generally, this second arrangement is referred to as an "off" configuration and the first arrangement is referred to as an "on" configuration. When the local magnetic fields produced by the tracking device 100 in response to an applied magnetic field are significantly nonzero, such as when the tracking device 100 is in the "on" configuration, the position of the tracking device 100 may be measured or identified by an MRI system in vivo.

Figure 2:
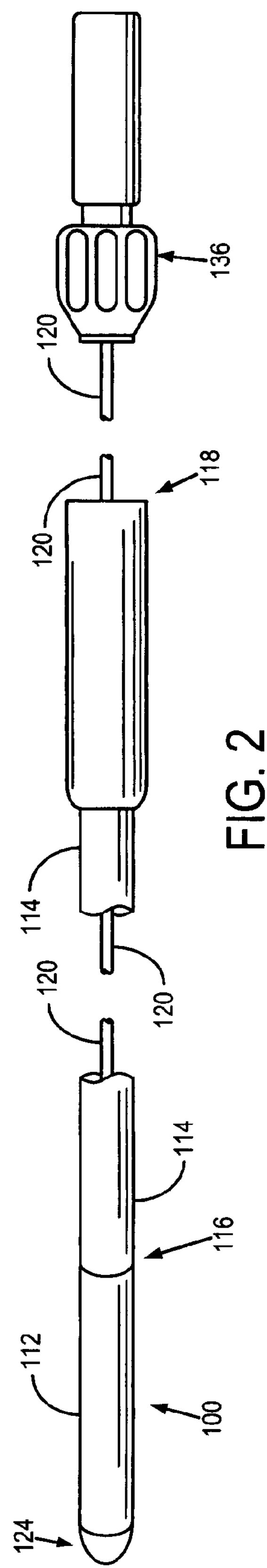
FIG. 2 is a plan view of an exemplary catheter system employing a tracking device in accordance with some embodiments of the present invention.
Figure 3:
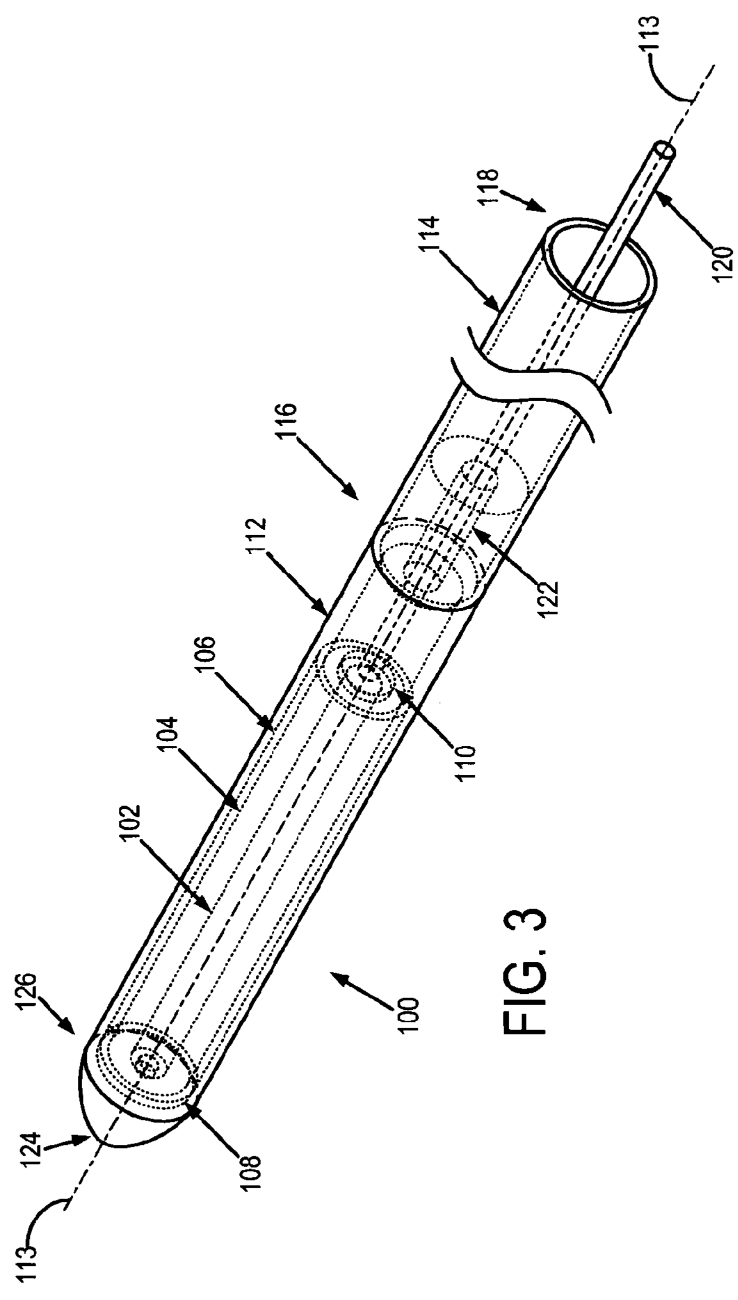
FIG. 3 is a perspective view of the exemplary tracking device that forms a part of the catheter device of FIG. 2.

An exemplary configuration of the tracking device 100 as it is coupled to a catheter system is illustrated in FIGS. 2 and 3. While this exemplary configuration is described with respect to the tracking of a catheter system, it will be appreciated by those skilled in the art that the tracking device 100 may similarly be coupled to other interventional instruments such as biopsy needles and ablation probes, such as those for thermal ablation and cryoablation. The tracking device 100 includes a cylindrical wire 102 about which a first annular sheath 104 is movably disposed. A second annular sheath 106 is movably disposed about the first annular sheath 104. A distal plate 108 may be coupled at one end of the cylindrical wire 102 to the cylindrical wire 102 and the second annular sheath 106, and a proximal plate 110 may be coupled at the other end of the cylindrical wire 102 to the first annular sheath 104.

The cylindrical wire 102 and the second annular sheath 106 are composed of a paramagnetic material, such as titanium; however, it will be appreciated by those skilled in the art that other suitable paramagnetic materials may also be used. The cylindrical wire 102 and second annular sheath 106 are preferably composed of materials having the same magnetic susceptibility; however, in some configurations the magnetic susceptibilities of the cylindrical wire 102 and second catheter sheath 106 may differ. The first annular sheath 104 is composed of a diamagnetic material, such as graphite; however, it will be appreciated by those skilled in the art that other suitable diamagnetic materials may also be used, such as bismuth. In general, it is preferable that the paramagnetic material have a substantially equal but opposite magnetic susceptibility as the diamagnetic material; however, this condition is not required for suitable operation of the tracking device 100. The cylindrical wire 102, first annular sheath 104, and second annular sheath 106 may be dimensioned such that they are flexible, which is an amenable attribute for use in a catheter.

Thus, in general, the tracking device 100 includes a first tracking member composed of paramagnetic materials and a second tracking member composed of diamagnetic materials. For the tracking device 100 configuration illustrated in FIGS. 3 and 4, the first tracking member is composed of the cylindrical wire 102 and second annular sheath 106, whereas the second tracking member is composed of the first annular sheath 104. It should be appreciated by those skilled in the art that the tracking device 100, which includes components composed of paramagnetic and diamagnetic materials, is visible with x-ray imaging. Thus, the tracking device may also be beneficial for interventional procedures that require or benefit from x-ray imaging, such as x-ray fluoroscopy and x-ray computed tomography.

The cylindrical wire 102, first annular sheath 104, and second annular sheath 106 are contained within a housing 112 that is composed, for example, of a biocompatible material such as a biocompatible polymer or medical grade polyvinyl chloride ("PVC"). The housing 112 forms a structure designed to hold the cylindrical wire 102, first annular sheath 104, and second annular sheath 106 in place while allowing these elements to move relative to each other along a common longitudinal axis 113. The housing 112 is also configured to provide a sterile operating environment for the tracking device components.

A catheter tube 114 extends from its distal end 116 proximally towards its proximal end 118 and is coupled at its distal end 116 to the housing 112 of the tracking device 100. The tracking device 100 is coupled to a wire 120 that extends away from the tracking device 100 through a lumen 122 in the housing 112 towards the proximal end 118 of the catheter tube 114. The wire 120 may be composed of a material having a magnetic susceptibility that is similar to tissue, such as copper or a polymer. A tip 124 is formed at the distal end 126 of the housing 112. The tip 124 is preferentially rounded so as to not damage vessel walls when in use; however, the tip 124 may also be shaped otherwise.

As noted, in some configurations, the tracking device 100 may be dimensioned so that it can be coupled to a catheter. For example, the tracking device 100 is dimensioned to be two French or larger, depending on the particular clinical application; however, with suitable manufacturing the tracking device may be dimensioned to be even smaller than two French.

Figure 4:
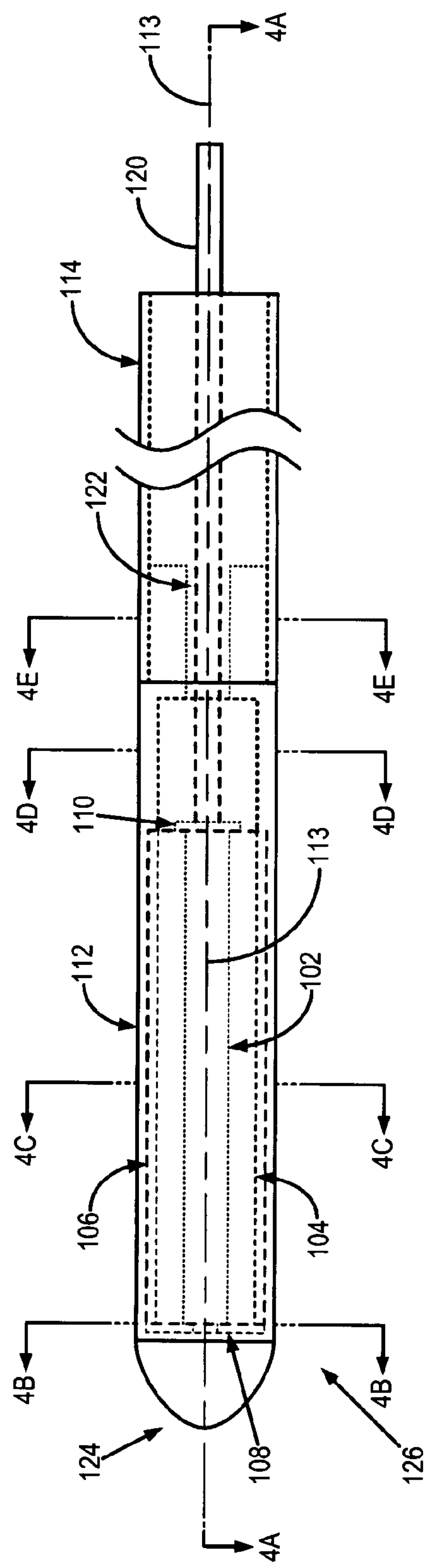
FIG. 4 is an elevation view of a portion of the tracking device of FIG. 2.
Figure 4A:
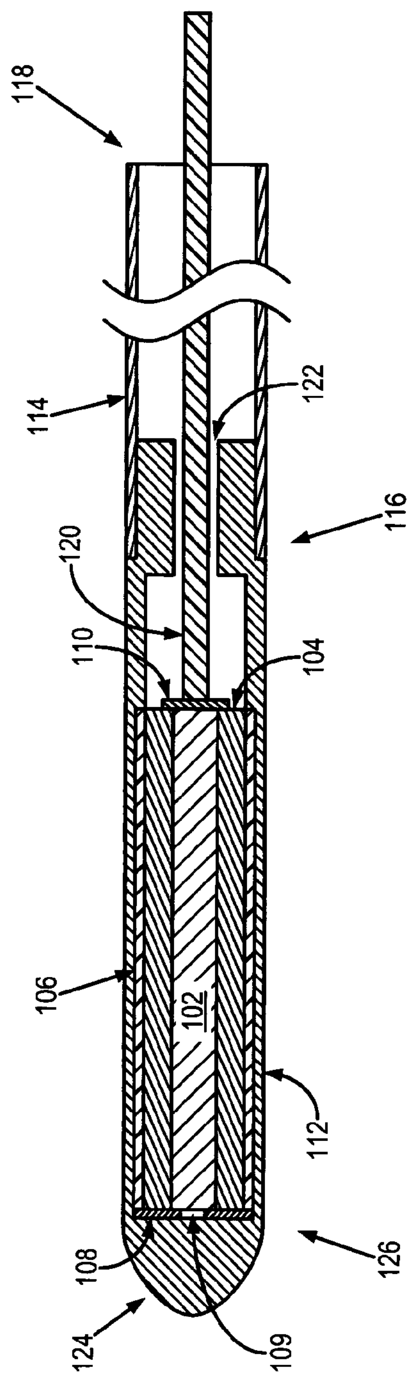
FIG. 4A is a cross-sectional view of the portion of the tracking device of FIG. 4 viewed along line 4A-4A.
Figure 4B:
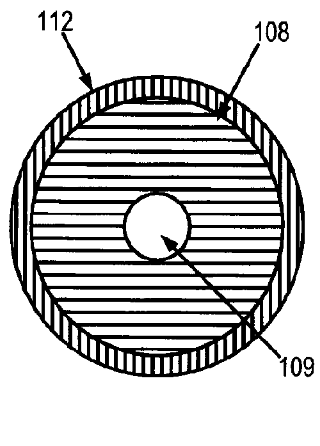
FIG. 4B is a cross-sectional view of the tracking device of FIG. 4 viewed along line 4B-4B.
Figure 4C:
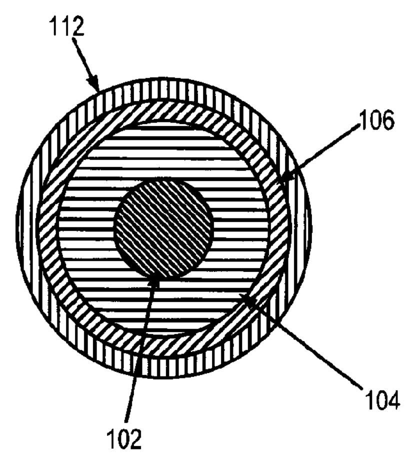
FIG. 4C is a cross-sectional view of the tracking device of FIG. 4 viewed along line 4C-4C.
Figure 4D:
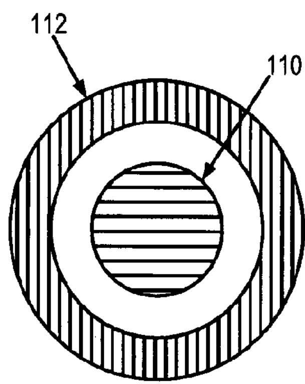
FIG. 4D is a cross-sectional view of the tracking device of FIG. 4 viewed along line 4D-4D.
Figure 4E:
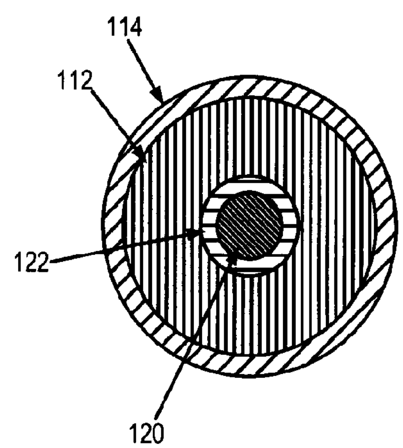
FIG. 4E is a cross-sectional view of the tracking device of FIG. 4 viewed along line 4E-4E.

Referring now to FIGS. 4 and 4A, the cylindrical wire 102, first annular sheath 104, and second annular sheath 106 have substantially similar lengths, and their relative thicknesses are dimensioned so that when the tracking device 100 is positioned within a magnetic field, such as the main magnetic field of an MRI system, the local magnetic fields produced by the respective components substantially cancel each other out, thereby resulting in the tracking device 100 having a substantially suppressed magnetic field disturbance.

The distal plate 108 may include a central aperture 109 so that the distal plate 108 may be coupled to the cylindrical wire 102 and the second annular sheath 106. In such an instance, the distal plate 108 may be dimensioned so that the outer diameter of the distal plate 108 is smaller than the outer diameter of the second annular sheath 106 to ensure a strong joint between the two components. The outer diameter of the distal plate may also be larger than the outer diameter of the first annular sheath 104 so that the distal plate 108 is not errantly coupled to the first annular sheath 104. To further ensure that the distal plate 108 is not errantly coupled to the first annular sheath 104, the inner diameter of the distal plate 108, that is the diameter of the central aperture 109, may be smaller than the inner diameter of the first annular sheath 104.

The proximal plate 110 may be dimensioned so that the outer diameter of the proximal plate 110 is smaller than the outer diameter of the first annular sheath 104 so that a strong joint between the two components can be formed. The distal and proximal plates 108, 110 may be composed of a material such as copper; however, a polymer material may also be used. The distal plate 108 may be coupled to the cylindrical wire 102 and second annular sheath 106 by way of an epoxy; however, other attachment means such as brazing may also be employed. The proximal plate 110 may be similarly coupled to the first annular sheath 104.

The tracking device 100 may be manipulated between the "on" and "off" configurations by way of a handle 136 that is coupled to the wire 120 at the proximal end of the wire 120. By manipulating the handle 136, the wire 120 may be translated axially along the longitudinal axis 113 of the tracking device 100. This translation of the wire 120 results in the first tracking member and the second tracking member being adjusted between the two arrangements of the "on" and "off" configurations of the tracking device 100. For example, translation of the wire 120 may result in the first annular sheath 104 being moved relative to the cylindrical wire 102 and second annular sheath 106, while in other configurations of the tracking device, translation of the wire 120 may result in one or both of the cylindrical wire 102 and second annular sheath 106 being moved relative to the first annular sheath 104.

In general, it will be appreciated by those skilled in the art that the desired effect of the tracking device 100 may be achieved by moving one or more of the tracking components relative to the others. Preferably, the components will be moved such that all of the diamagnetic components and all of the paramagnetic components are displaced relative to each other. Such an arrangement provides the maximal effect; however, a measurable alteration of the magnetic field of an MRI can be achieved with the displacement of only one component relative to the others.

It is preferable that the magnetically susceptible components be configured to retract proximally away from the distal end 126 of the tracking device 100 so that the components remain within the housing 112. This configuration allows for the inner components in the tracking device 100 to be kept separate from the patient, thereby maintaining sterility of these components and avoiding any toxicity that may occur by exposure of the body to the materials used for the inner components of the tracking device 100. It should be appreciated by those skilled in the art, however, that the tracking device 100 can also be configured such that the magnetically susceptible components be translated distally into an enclosed void at the tip of the housing 112.

In some configurations the wire 120 may be composed of a paramagnetic material, or contain a paramagnetic tip portion, and may replace the cylindrical wire 102. In such configurations, the first annular sheath 104 may be coupled to the interior of the housing 112 at the distal end of the first annular sheath 104. Thus, in such configurations the wire 120 and second annular sheath 106 may be coupled together such that translation of the wire 120 results in translation of the second annular sheath 106 as well. For example, the wire 120 may be coupled to the second annular sheath 106 by way of a washer that is, for example, brazed to the wire 120 and second annular sheath 106.

Referring briefly to FIGS. 4B-4E, in cross-section the components of the tracking device 100, including the housing 112; optional distal and proximal plates 108, 100; cylindrical wire 102; first and second annular sheaths 104, 106; and wire 120 are all substantially concentric and aligned along a common longitudinal axis.

Figure 5A:
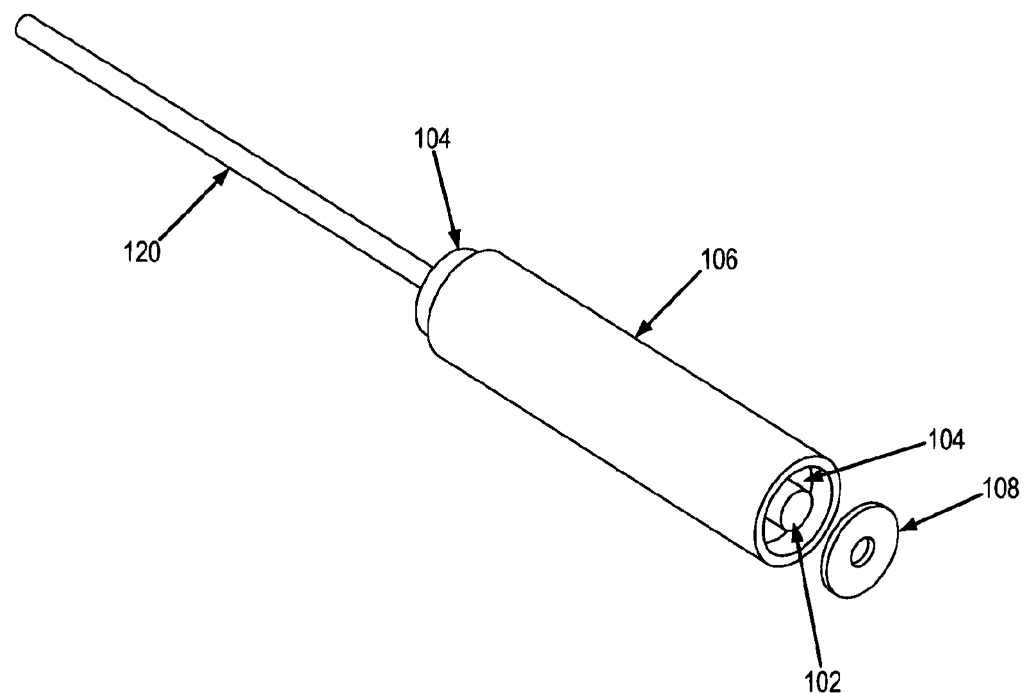
FIG. 5A is a perspective view of paramagnetic and diamagnetic components of the tracking device of FIG. 3, in which a coupling of two components by way of a distal plate is illustrated.

Referring briefly to FIG. 5A, the cylindrical wire 102 and second annular sheath 106 may be coupled together by way of the distal plate 108. The distal plate 108 may be shaped like an annular disc so that the edges of the distal plate 108 may be coupled to both the cylindrical wire 102 and second annular sheath 106 by way of brazing.

Figure 5B:
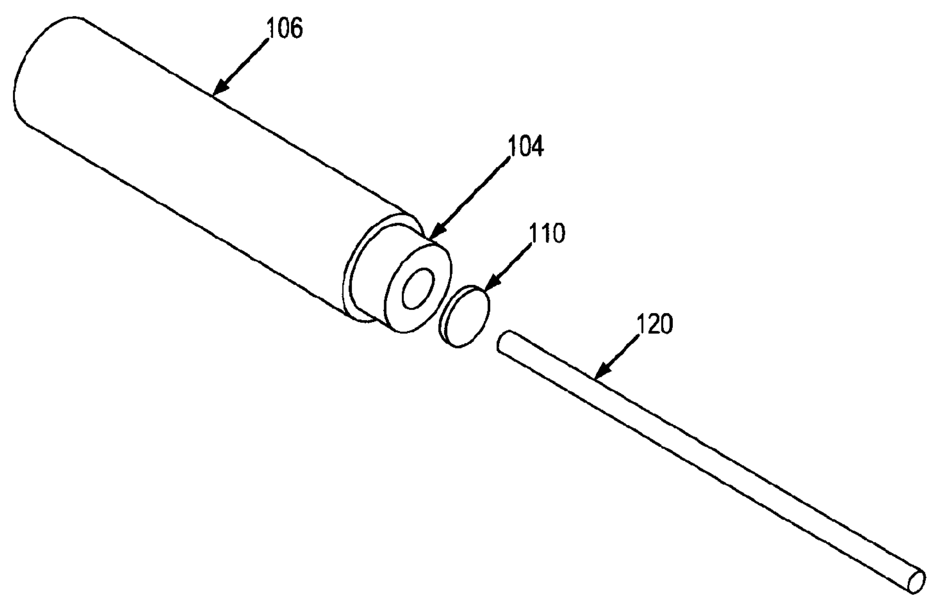
FIG. 5B is a perspective view of paramagnetic and diamagnetic components of the catheter tracking device of FIG. 3, in which a coupling of one of the components to a wire by way of a proximal plate is illustrated.

Referring briefly now to FIG. 5B, the first annular sheath 104 may be coupled to the wire 120 by way of the proximal plate 110. When the first annular sheath 104 is composed of a non-metallic material, the first annular sheath 104 and wire 120 may be coupled to the proximal plate 110 using an epoxy. However, when the first annular sheath 104 is composed of a metallic material, then brazing can be used to couple the first annular sheath 104 and wire 120 to the proximal plate 110.

Figure 6A:
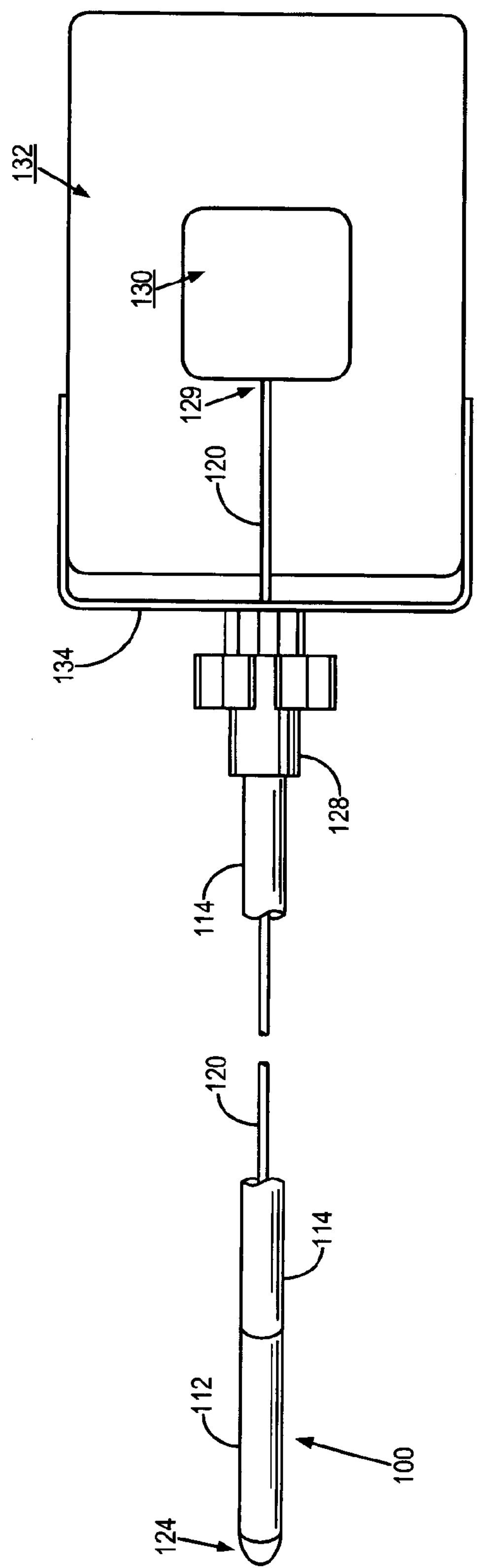
FIG. 6A is a plan view of another exemplary catheter device, which includes a driver, employing a tracking device in accordance with some embodiments of the present invention.
Figure 6B:
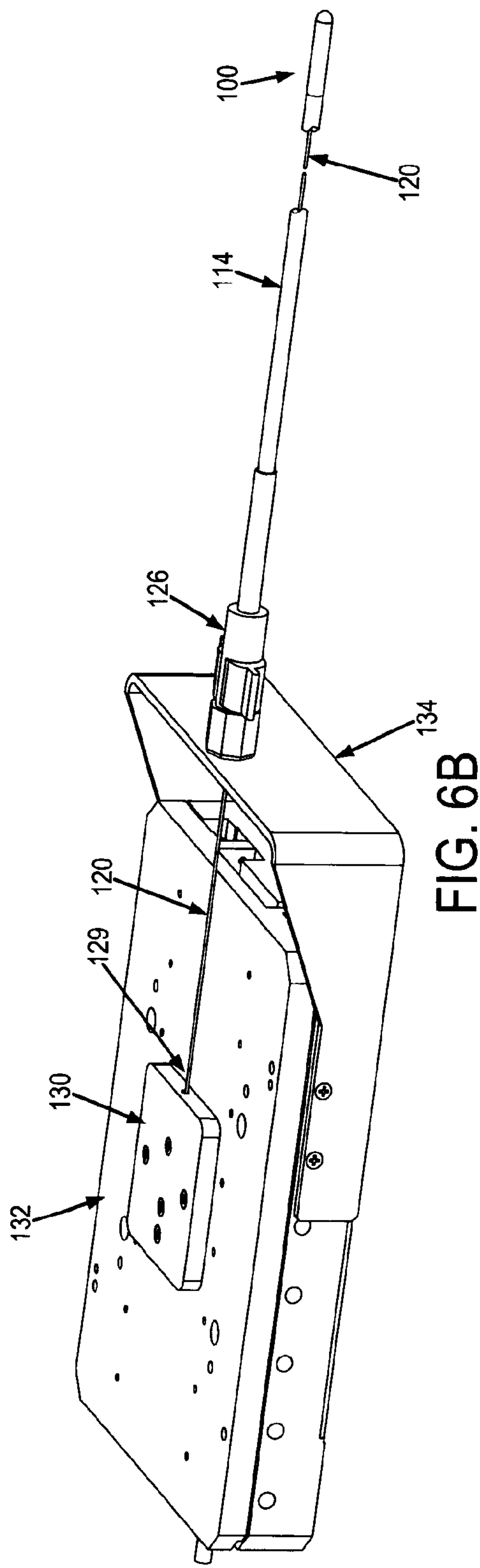
FIG. 6B is a perspective view of the exemplary catheter device of FIG. 6A.

Another exemplary configuration of the provided tracking device 100 as it is coupled to a catheter system is illustrated in FIGS. 6A and 6B. The tracking device 100 may be coupled to a catheter tube 114 that is coupled to a catheter connector 128. The wire 120 may extend through the catheter tube 114 and catheter connector 128, with its proximal end 129 coupled to a wire holder 130. The wire holder may be coupled to a driver 132, such as a piezoelectric motor. MRI compatible piezoelectric motors are known in the art. For example, an M-683 PILine precision micro translation stage piezomotor (Physik Instrumente, GmbH & Co. KG; Karlsruhe, Germany) may be used and programmed to translate the wire 120 by a few millimeters with a 0.1 micrometer resolution. The catheter connector is coupled to a driver holder 134, which holds the driver 132 in place during operation. The driver holder 134 may be composed of, for example, PVC. Similar to the configuration of the tracking device 100 illustrated in FIG. 2, the tracking device 100 may be manipulated between its "on" and "off" configurations by way of the driver 132, which can be operated to translate the wire 120.

Figure 7A:
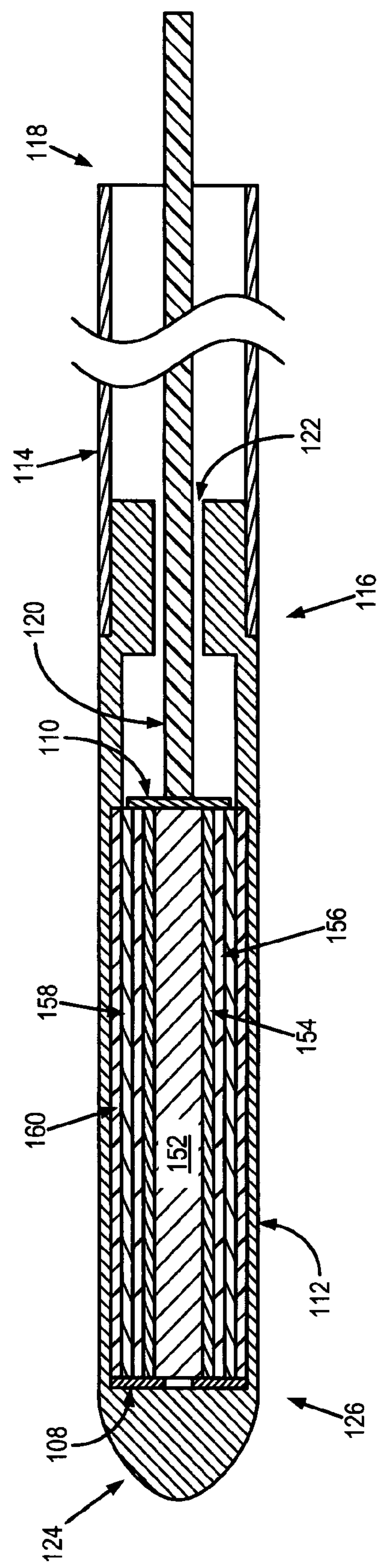
FIG. 7A is a cross-sectional view of the tracking device of FIG. 7 viewed along line 7A-7A.
Figure 7:
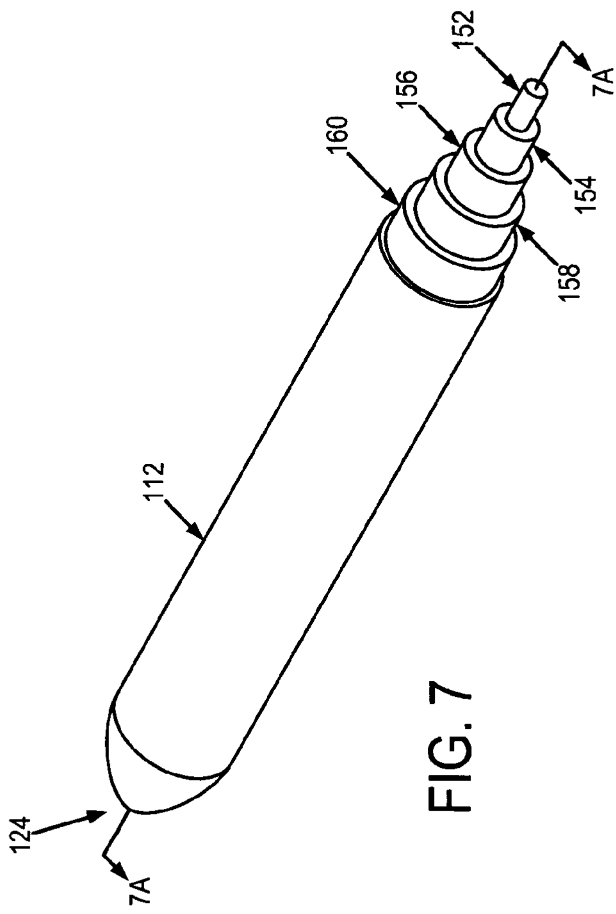
FIG. 7 is a perspective view of another configuration of an exemplary tracking device that forms a part of the catheter device of FIG. 2, in which the tracking device includes five concentrically layered components that are partially retracted for illustrative purposes.

While the tracking device 100 configuration illustrated in FIGS. 4 and 4A include three magnetically susceptible components (102, 104, 106), it will be appreciated by those skilled in the art that additional concentrically layered components can be incorporated into the tracking device 100 to provide different local magnetic field configurations produced by the tracking device 100 in a magnetic field. For example, and referring now to FIGS. 7 and 7A, the tracking device 100 can include more than three, such as five, magnetically susceptible components. The tracking device 100 may include a cylindrical wire 152 about which a first annular sheath 154 is movably disposed. This first annular sheath 154 can be movably positioned within a second annular sheath 156, which in turn may be positioned within a third annular sheath 158, which in turn may be positioned within a fourth annular sheath. In general, any number of concentrically layered components of alternating magnetic susceptibilities may be used.

While it is preferable that an odd number of components be used with the central component being composed of a paramagnetic material, it will be appreciated by those skilled in the art that other arrangements are possible. For example, an even number of components may be used, such as two components, and components having like or similar magnetic susceptibilities may be adjacent to each other. Moreover, the central component need not be composed of a paramagnetic material, but may be composed of a diamagnetic, or magnetically neutral, material. For the configuration of the tracking device 100 illustrated in FIGS. 7A and 7B, the first tracking member is composed of the cylindrical wire 152, the second annular sheath 156, and the fourth annular sheath 160, whereas the second tracking member is composed of the first annular sheath 154 and third annular sheath 158. Thus, generally, the cylindrical wire 152, the second annular sheath 156, and the fourth annular sheath 160 are composed of a paramagnetic material, whereas the first annular sheath 154 and third annular sheath 158 are composed of a diamagnetic material. In some configurations, it may be beneficial to move individual components within a tracking member relative to each other. For example, the cylindrical wire 152, second annular sheath 156, and fourth annular sheath 160 may be configured so that they can be moved individually relative to each other instead of in unison. When more than three concentric components are present in the tracking device 100, it will be appreciated by those skilled in the art that a distal plate 108 and proximal plate 110 may similarly be used to couple components having similar or dissimilar magnetic susceptibilities.

Figure 8:
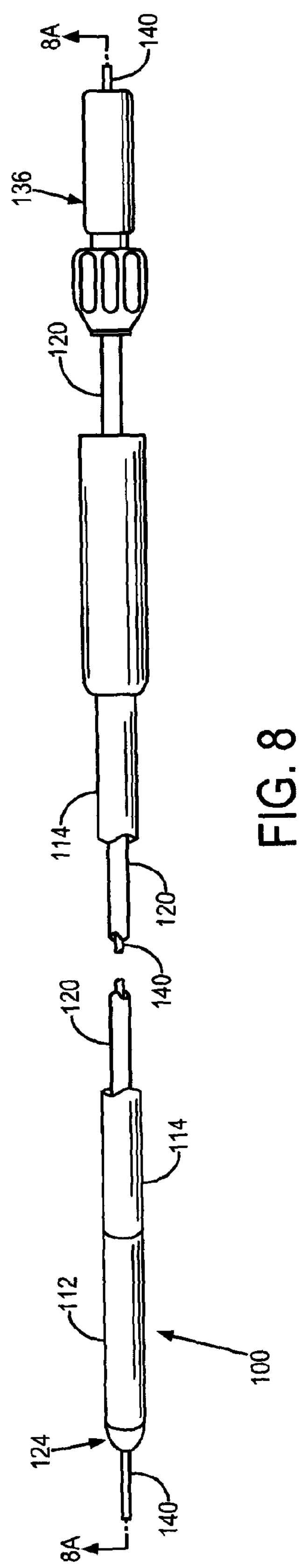
FIG. 8 is a plan view of another exemplary catheter system employing a tracking device in accordance with some embodiments of the present invention, in which the tracking device includes a central lumen through which an interventional tool or contrast agent may be passed.
Figure 8A:
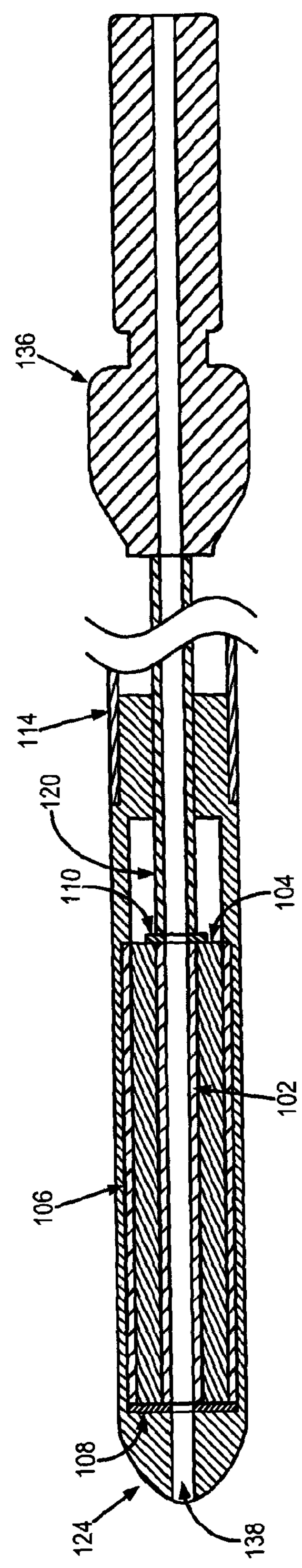
FIG. 8A is a cross-sectional view of the tracking device of FIG. 8 viewed along line 8A-8A.

Referring now to FIGS. 8 and 8A, in some configurations the tracking device 100 includes a central lumen 138 extending from the tip 124 of the tracking device proximally through the tracking device 100. For example, the central lumen 138 extends through the housing 112, the distal plate 108, the cylindrical wire 102, the proximal plate 110, the wire 120, and the handle 136. The central lumen 138 is dimensioned so that an interventional tool 140 can be provided through the central lumen 138. Exemplary interventional tools 140 include catheter guidewires, ablation probes, balloon catheters, stents, or needles. A liquid contrast agent, such as gadolinium-DTPA or a radioopaque dye, may also be provided through the central lumen 140 to aid in visualization of the tissue and microvasculature beyond the tip 124 of the tracking device 100.

The materials and dimensions of the magnetically susceptible components are selected by, for example, first measuring the relative magnetic susceptibilities of the paramagnetic and diamagnetic materials using, for example, an Evans balance. The readings from an Evans balance are, for example, 953+/−1 percent for titanium and −745+/−1 percent for graphite. These measured parameters may then be used in an optimization procedure to design the component thicknesses that minimize the magnetic fields outside of the tracking device 100 when the ends of the components are aligned.

A magnetostatic simulation may be used, with the magnetic field surrounding the components computed for each iteration of the optimization. A cost function that is the sum of the absolute values of the magnetic field offsets at points within a region-of-interest adjacent to the tracking device 100 is used during this optimization. An exemplary region-of-interest may be 4.1 millimeters by 2 millimeters in size. The diameter of the outer paramagnetic layer may be fixed to a desired size, such as 3 millimeters, where then the free parameters to be optimized are the outer diameters of other components. The cost function is systematically computed over a range, and a minimum in the cost function is found. For the three-layer configuration of the tracking device 100, such as the one illustrated in FIG. 4, an exemplary set of outer diameters is as follows: 3 millimeters for the second annular sheath 106, 2.43 millimeters for the first annular sheath 104, and 1.11 millimeters for the cylindrical wire 102. These diameters are specific to the measured magnetic properties noted above, but it will be appreciated by those skilled in the art that the same optimization procedure may be used with other materials, yielding different dimensions, and that the optimization may be extended to devices with more than three layers.

Figure 9A:
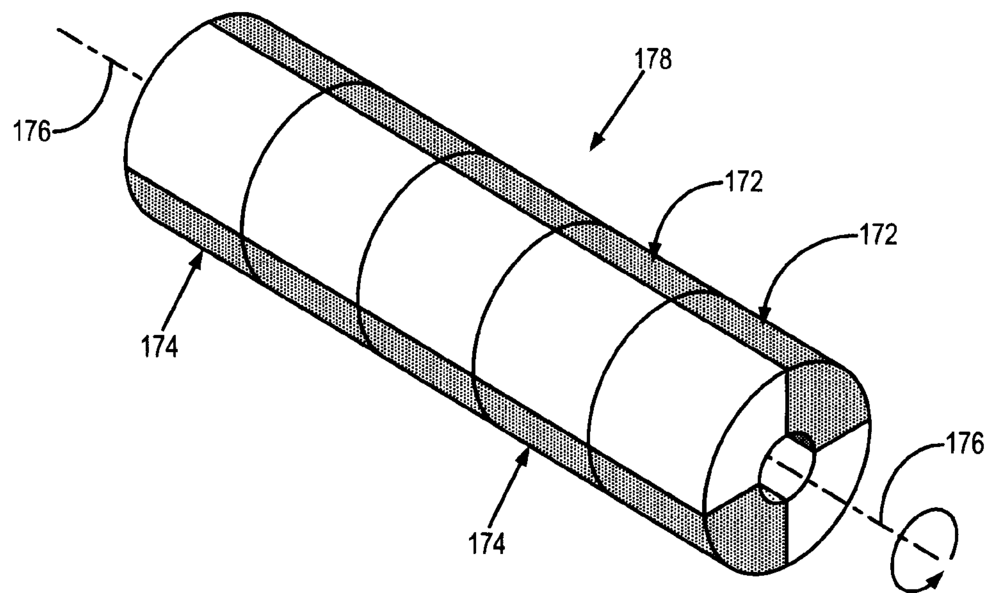
FIG. 9A is a perspective view of a configuration of a tracking device in accordance with some embodiments of the invention, in which the tracking device includes two tracking members that are composed of a plurality of radial sectors.
Figure 9B:
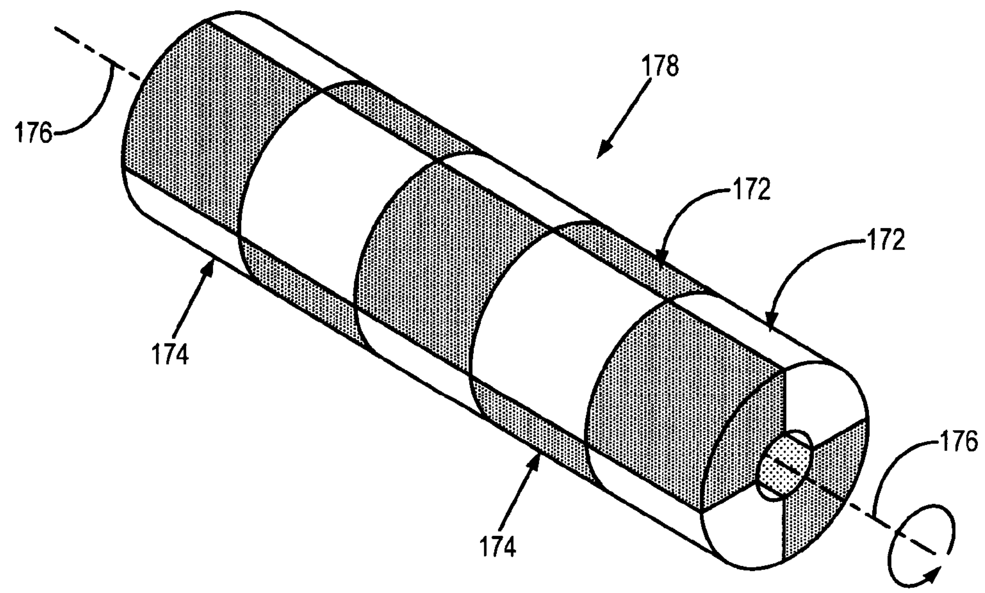
FIG. 9B is a perspective view of the tracking device of FIG. 9A in which the tracking device is in an "off" configuration.

As described above, the first and second tracking members that form a part of the tracking device 100 may include a plurality of concentric cylindrical or annular components arranged about a common axis. In other configurations, however, the first and second tracking members may include components shaped and arranged in different configurations. For example, referring to FIGS. 9A and 9B, an alternative configuration of a first and second tracking member is illustrated. Such tracking members are formed as a plurality of radial sectors 172 arranged to form a plurality of annular discs 174. The annular discs 174 are aligned along a longitudinal axis 176 to form an annular structure 178. Preferably, each annular disc 174 includes at least one radial sector 172 associated with the first tracking member and at least one other radial sector 172 associated with the second tracking member. Generally, the first tracking member is composed of those radial sectors 172 having a first magnetic susceptibility, and the second tracking member is composed of those radial sectors 172 having a second magnetic susceptibility that is different that the first magnetic susceptibility. A subset of the annular discs 174 may be rotated about the longitudinal axis 176 relative to the others, so that the radial sectors 172 having similar magnetic susceptibilities move through a first arrangement, such as the one illustrated in FIG. 9A, and a second arrangement, such as the one illustrated in FIG. 9B. The first arrangement illustrated in FIG. 9A is an "off" configuration, whereas the second arrangement illustrated in FIG. 9B is an "on" position. The annular discs 174 may be rotated, for example, by the wire 120 which may be configured to engage each of the annular rings 174 while extending through an aperture 180 in the annular structure 178. In such a configuration, it may be beneficial for the wire 120 to be composed of a material having magnetic susceptibility substantially similar to tissue.

Having described the general structure of the tracking device 100, and various exemplary configurations thereof, a description of a general operation of the tracking device 100 is now provided. By way of example, the tracking device 100 may be used during the crossing of an occluded blood vessel using an interventional instrument that incorporates the tracking device 100 at the tip of the instrument. Magnetic resonance images may be acquired during the process of pushing the instrument through the proximal side of the occlusion, along the track of the occluded vessel, and out of the distal side of the occlusion. By alternately acquiring images with the tracking device 100 in its "on" and "off" configurations, the position of the tracking device 100 and instrument can be accurately determined while magnetic resonance images, depicting the tissue immediately adjacent to the instrument tip can be acquired with substantially no distortion from susceptibility artifacts. Accurate tracking device 100 location measurements can be indicated on the acquired images of the section of occluded vessel that is in the immediate path of the tracking device 100. This gives the clinician confidence that the device is on course while the next few millimeters of occlusion are crossed, after which a new location measurement and corresponding, minimally distorted anatomical image of the occluded vessel are acquired.

To quickly and accurately measure the location of the tracking device 100, several different types of magnetic resonance images may be obtained. For example, by employing the so-called "white marker" phenomenon described in published U.S. patent application Ser. No. 11/257,415, images can be acquired in which signal is received only from the immediate vicinity of the tracking device 100, with greatly suppressed signal from all other locations. The position of the tracking device 100 can thus be quickly estimated from projection images having coarse spatial resolution. Then, a measurement with higher spatial resolution can be performed, limiting the field-of-view to the volume estimated from the projection images. This second acquisition can be performed with the white-marker imaging mentioned above, with conventional gradient-echo imaging, or with any suitable magnetic resonance imaging method that results in images influenced by the device in the "on" configuration.

In some embodiments, a two-step process is used to determine the location of the tracking device 100. In the first step, an approximate location of the tracking device 100 is computed from projection images. With the device in the "on" configuration, where substantially maximal magnetic field disturbance is produced, the aforementioned white-marker technique may be used to determine the location of the tracking device with an accuracy of approximately plus-or-minus 0.5 centimeters. Such a method includes computing the location of signal maxima in images acquired with the white marker method. In the second step, a two-dimensional slice location is positioned at the location computed in the preceding step, and a two-dimensional image is acquired using, for example, a slice-selective gradient echo pulse sequence. The resulting image is then input into a fitting algorithm described below. These two stages can be alternated rapidly in order to continuously update the position displayed to the operator on the console, or physician in the operating room.

To accurately measure the position of the tracking device 100, the imaging data can be fitted numerically to a model of the effect of the tracking device 100 on a magnetic resonance image. Parameters relating to the configuration of the paramagnetic and diamagnetic components relative to one another will be known and do not need to be derived by fitting. Thus, the parameters to be fit are the spatial coordinates of the tracking device 100 as well as the orientation of the tracking device 100 relative to the main magnetic field of the MRI system.

Two images are used in the numerical fit: one depicting the tracking device 100 in the "on" configuration, and one depicting the tracking device 100 in the "off" configuration. Preferably, these images are reconstructed from image data that was acquired as close in time as is feasible. The phase difference between these two images is calculated and used as input to the fitting process.

The numerical model fitting generally proceeds as follows. The approximate tip position and tracking device angle relative to the main magnetic field are input as the starting point in the fit. A simulation of the MRI scanning process (excitation, application of gradients, data sampling) is used to compute the images that would result from the device, in both the "on" and "off" configurations, within a uniform medium. The phase difference between these two simulated images is computed. A cost function is then computed for the current, or initial, position of the tracking device 100. In some embodiments, this cost function includes the sum-of-squares of the difference between the real and simulated phase-difference images. The process is then iterated by an optimization solver, with the cost function computed for an array of positions until a minimum in the cost function is found. The position that corresponds to this minimum is identified and stored as the computed position.

For accurate computation of the position of the device tip, it is useful to have information about the orientation of the device relative to the main magnetic field of the MRI system. When the tracking device 100 is in the on position, two regions of signal disturbance are generated: one at the distal end of the tracking device, and one at the proximal end of the tracking device. These regions of signal disturbance appear in images produced with the MRI system, and the angle between these disturbances can be used as an estimate of the angle of the device relative to the main magnetic field. This orientation information can then be used as an input to a fitting algorithm used to compute the position of the tracking device 100.

To enable the acquisition of images with the tracking device 100 in both the "on" and "off" configurations in rapid succession, an actuator, such as the driver 132 described above, can be used to rapidly and accurately actuate the tracking device 100 between the "on" and "off" configurations. In some embodiments, this actuator may be synchronized with the MRI system such that the tracking device 100 is actuated to the "off" configuration from the "on" configuration in a minimal time interval, such as twenty milliseconds, after the acquisition of the first image. This synchronization can be accomplished by triggering the actuator by a transistor-transistor logic ("TTL") pulse that is provided by the MRI system at the start of each iteration of a pulse sequence. As described above, however, a driver 132 need not be used to manipulate the tracking device 100; rather, manual manipulation of the tracking device 100 can similarly be implemented.

By alternately acquiring images with the paramagnetic and diamagnetic components of the tracking device 100 in their "on" and "off" positions, the location of the tracking device 100 can be accurately determined, while magnetic resonance images, showing the tissue immediately in front of and surrounding the tracking device can be acquired with minimal distortion. These accurate tracking device location measurements can be optionally overlaid on the MR image of the region-of-interest, such as an occluded vessel, that is in the immediate path of the device. This provides the clinician confidence that the device is on course for the next few millimeters of occlusion crossing, after which a new tip-location measurement and corresponding, minimally distorted, anatomical image of the occluded vessel may be acquired.

The present invention has been described in terms of one or more preferred embodiments, and it should be appreciated that many equivalents, alternatives, variations, and modifications, aside from those expressly stated, are possible and within the scope of the invention.

The invention claimed is:

1. A tracking device configured to be coupled to an interventional medical device to track a position of the interventional medical device during an interventional medical procedure using a magnetic resonance imaging (MRI) system, the tracking device comprising:

a first tracking member having a first magnetic susceptibility and configured to be coupled to an interventional medical device;

a second tracking member having a second magnetic susceptibility different than the first magnetic susceptibility and configured to be coupled to the interventional medical device;

wherein the first tracking member and the second tracking member are configured to adjust relative to each other to adjust the tracking device between a first arrangement and a second arrangement; and wherein the first magnetic susceptibility and the second magnetic susceptibility are selected such that when the tracking device is positioned within a magnetic field of an MRI system:

when the tracking device is arranged in the first arrangement the tracking device produces a local magnetic field that is measurable by the MRI system; and when the tracking device is arranged in the second arrangement the tracking device produces a local magnetic field that is reduced with respect to the local magnetic field produced by the tracking device in the first arrangement.

2. The tracking device as recited in claim 1 further comprising a wire coupled to at least one of the first tracking member and the second tracking member for adjusting the tracking device between the first arrangement and the second arrangement.

3. The tracking device as recited in claim 1 further comprising:

a driver;

a wire extending along an axis from a distal end to a proximal end, the distal end being coupled to the at least one of the first tracking member and the second tracking member, and the proximal end being coupled to the driver; and wherein the driver is configured to actuate the wire such that one of the first tracking member and the second tracking member is moved relative to the other, thereby adjusting the tracking device between the first arrangement and the second arrangement.

4. The tracking device as recited in claim 1 in which the first tracking member comprises a plurality of paramagnetic radial sectors and the second tracking member comprises a plurality of diamagnetic radial sectors, the paramagnetic radial sectors and diamagnetic radial sectors being configured to rotate about an axis of rotation.

5. The tracking device as recited in claim 1 in which the first tracking member comprises at least one paramagnetic component and the second tracking member comprises at least one diamagnetic component.

6. The tracking device as recited in claim 5 in which the at least one paramagnetic component and the at least one diamagnetic component are concentrically arranged about an axis.

7. The tracking device as recited in claim 6 in which the at least one paramagnetic component and the at least one diamagnetic component are arranged about the axis in alternating layers of paramagnetic and diamagnetic components.

8. The tracking device as recited in claim 6 in which:

the at least one paramagnetic component and the at least one diamagnetic component have substantially similar lengths;

ends of the at least one paramagnetic component and the at least one diamagnetic component are substantially aligned when the tracking device is arranged in the second arrangement; and ends of the at least one paramagnetic component and the at least one diamagnetic component are not aligned when the tracking device is arranged in the first arrangement.

9. The tracking device as recited in claim 6 in which the at least one paramagnetic component comprises three concentric paramagnetic components, and the at least one diamagnetic component comprises two diamagnetic components.

10. The tracking device as recited in claim 8 in which each of the three concentric paramagnetic components and each of the two diamagnetic components are configured to move independently of the others when the first tracking member and the second tracking member are adjusted relative to each other.

11. The tracking device as recited in claim 5 in which the at least one paramagnetic component includes a paramagnetic wire extending along an axis from a proximal end to a distal end and a paramagnetic sheath coupled to the paramagnetic wire and extending along the axis from a proximal end to a distal end.

12. The tracking device as recited in claim 11 in which the at least one diamagnetic component includes a diamagnetic sheath extending along the axis from a proximal end to a distal end, the diamagnetic sheath being movably positioned between the paramagnetic wire and the paramagnetic sheath.

13. The tracking device as recited in claim 12 further comprising a plate coupled to the diamagnetic sheath and structured to engage a wire that when actuated axially displaces the diamagnetic sheath along the axis of the diamagnetic sheath.

14. The tracking device as recited in claim 12 further comprising an annular plate structured to couple the paramagnetic wire to the paramagnetic sheath.

15. The tracking device as recited in claim 14 further comprising a wire coupled to the annular plate, the wire being configured to axially displace the paramagnetic wire and paramagnetic sheath when actuated.

16. A catheter device for use with a magnetic resonance imaging (MRI) system, the catheter device comprising:

a tracking device comprising:

a first annular component having a first magnetic susceptibility;

a second annular component having a second magnetic susceptibility different than the first magnetic susceptibility;

a catheter coupled to the tracking device;

a wire coupled to the tracking device and extending along an axis from a proximal end to a distal end through a lumen in the catheter;

wherein the first annular component and the second annular component are moved relative to each other when the wire is actuated, thereby altering local magnetic fields produced by the tracking device when the tracking device is positioned in a magnetic field of an MRI system.

17. The catheter device as recited in claim 16 in which the first and second annular components have substantially similar lengths, and in which the local magnetic fields produced by the tracking device produce a magnetic field disturbance measurable by the MRI system when ends of the first and second annular components are not aligned.

18. The catheter device as recited in claim 16 in which the first annular component is movably positioned within the second annular component, and in which the wire extends through the first annular component and is coupled to the second annular component at a distal end of the second annular component.

19. The catheter device as recited in claim 16 in which the tracking device further comprises a cylindrical component movably positioned within the first annular component, the cylindrical component having a similar magnetic susceptibility as the second annular component; and in which the wire is coupled to at least one of the cylindrical component and the first annular component.

20. The catheter device as recited in claim 16 in which the wire includes a lumen extending from the proximal end to the distal end of the wire, the lumen being dimensioned to receive at least one of an interventional tool and a contrast agent.

* * * * *

UNITED STATES PATENT AND TRADEMARK OFFICE

CERTIFICATE OF CORRECTION

PATENT NO. : 8,676,295 B2
APPLICATION NO. : 13/518160
DATED : March 18, 2014
INVENTOR(S) : Cunningham et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 76 days.

Signed and Sealed this
Twenty-ninth Day of September, 2015

Michelle K. Lee

Michelle K. Lee
*Director of the United States Patent and Trademark Office*